United States Patent
Tellier et al.

(10) Patent No.: US 7,795,182 B2
(45) Date of Patent: Sep. 14, 2010

(54) METHOD FOR MAKING BIOCHIPS

(75) Inventors: Charles Tellier, Notre Dame des Landes (FR); Muriel Pipelier, Nantes (FR); Didier Dubreuil, Port Saint Pere (FR); Bruno Bujoli, Suce sur Erdre (FR); Daniel Talham, Gainesville, FL (US)

(73) Assignees: Centre National de la Recherche Scientifique (C.N.R.S.), Paris (FR); Universite de Nantes, Nantes (FR); University of Florida, Gainesville, FL (US)

( * ) Notice: Subject to any disclaimer, the term of this patent is extended or adjusted under 35 U.S.C. 154(b) by 441 days.

(21) Appl. No.: 10/522,161

(22) PCT Filed: Jul. 22, 2003

(86) PCT No.: PCT/FR03/02318

§ 371 (c)(1),
(2), (4) Date: Sep. 30, 2005

(87) PCT Pub. No.: WO2004/011401

PCT Pub. Date: Feb. 5, 2004

(65) Prior Publication Data

US 2006/0134717 A1 Jun. 22, 2006

(30) Foreign Application Priority Data

Jul. 25, 2002 (FR) .................................. 02 09456

(51) Int. Cl.
*C40B 50/18* (2006.01)
(52) U.S. Cl. ............................... 506/32; 506/40; 435/6; 435/7.92
(58) Field of Classification Search ....................... None
See application file for complete search history.

(56) References Cited

U.S. PATENT DOCUMENTS 6,936,461 B2 * 8/2005 Gagna ..................... 435/287.2
7,097,974 B1 * 8/2006 Stahler et al. .................. 435/6

FOREIGN PATENT DOCUMENTS

WO     WO 03/046508 A2 *  6/2003

OTHER PUBLICATIONS

Melissa A. Petruska, Gail E. Fanucci, Daniel R. Talham, Organic/Inorganic Langmuir-Blodgett films based on metal phosphonates 2: Zirconium phosphonate-based alternating layer films, 1998, Elsevier Science S.A., Thin Solid Films 327-329, (1998), pp. 131-135.*

(Continued)

*Primary Examiner*—Christopher Low
*Assistant Examiner*—Christopher M. Gross
(74) *Attorney, Agent, or Firm*—Young & Thompson

(57) ABSTRACT

A method for immobilizing biological polymers such as DNA or proteins, on a solid support, by ionocovalent bond, for making biochips, and the resulting chips obtained by the method.

10 Claims, 3 Drawing Sheets

OTHER PUBLICATIONS

Brousseau et al (1994 ACS Symposium Series 561:60-70).*

Bellezza F. et al.:, "Zirconium phosphate and modified zirconium phosphates as supports of lipase. Preparation of the composites and activity of the supported enzyme." Langmuir vol. 18, 2002-pp. 8737-8742, XP002240673 p. 8737, right-hand column, paragraph 2, p. 8738, left-hand column, paragraph 5, p. 8739, en particulier colonne de gauche, dernier paragraphe p. 8740, colonne de gauche, dernier paragraphe.

Kumar C V et al:, "Proteins immobilized at the galleries of layered 'alpha1-zirconium phosphate: Structure and activity studies" Journal of the American Chemical Society Feb. 9, 2000, United States, vol. 122, No. 5, Feb. 9, 2000 92000-02-09), pp. 830-837, XP002266758 ISSN: 0002-7863 p. 830-p. 831 Chart 1.

Xu X H et al:, "Immobilization of DNA on an Aluminum (III) Alkanebisphosphonate Thin Film With Electrogenerated Chemilumenescent Detection" Journal of the American Chemical Society, American Chemical Society, Washington, DC, US, vol. 116, 1994, pp. 8386-8387, XP00929137 ISSN: 0002-7863, p. 8386 figure 1.

Benitez I.O. et al:, "Monolayers as models for supported catalysts: zirconium phosphonate films containing manganese (III) porphyrins" J. Am. Chem. Soc., vol. 124, 2002, pp. 4363-4370, XP002240672 cited in the application p. 4364, left-hand column, paragraph 2 "scheme 1".

Database WPI, Section Ch, Week 200170 Derwent Publications Ltd., London, GB; AN 2001-608992, XP002240674 & JP 2001 178470 A (Fuji Photo Film Co Ltd), Jul. 3, 2001 abstract.

Ihara T. et al.:, "DNA separation using Zr(IV)-loaded resin through ligand exchange", Analytical Sciences, vol. 17, 2001, p. il229 XP00801581 p. il229 figure 2.

* cited by examiner

METHOD FOR MAKING BIOCHIPS

The invention relates to a method of immobilizing DNA, proteins or oligo- or poly-saccharides on a solid support for the manufacture of biochips, and the chips obtained by this method.

Various methods are today used for the manufacture of DNA chips. According to a first method, oligonucleotides are synthesized directly on the support after covalent anchoring of a precursor (Affymetrix system, Niemeyer and Blohm Angew; Chem. Int. Ed. 1999, 38, 2865-2869), which leads to expensive chips. In addition, the supplier does not provide all the details of the sequences of the immobilized oligonucleotides.

According to a second approach, the oligonucleotides are presynthesized, biotinylated and then deposited on a plate activated by a layer of streptavidin. The coupling is effected via specific non-covalent biotin-streptavidin interactions, streptavidin being a protein having the disadvantage of having only moderate stability. When the chips are constituted by cDNA fragments, these fragments are generally immobilized by adsorption on a layer of aminosilane or polylysine. This last-mentioned strategy often poses problems of repeatability and surface homogeneity associated with the difficulty of controlling the quality of the polylysine film and the stability thereof.

According to a third route, the oligonucleotides or cDNA are anchored to the support by means of covalent coupling, via an organic chemical linkage. This requires (a) surface functionalization by chains having reactive terminals, for example, activated carboxylic acid functions, (b) modification of the oligonucleotides or cDNA in the 5' position by a function, for example, a primary amine, capable of reacting with the above-mentioned terminals. These are "turnkey" products which are relatively expensive, making it necessary to buy suitably modified oligonucleotides. These approaches are described in particular in patent application WO 01/42 495.

DNA chip technology is also discussed in the review article of Wang, Nucleic Acids Res., 2000, 28(16):3011-3016.

In parallel with this, chips have been developed on which biopolymers other than DNA, for example proteins or peptides, were immobilized.

That technology was developed principally by adapting DNA chip technology (cf, for example, application WO 93/22 680 of Affymax).

A method of fixing proteins by covalent bonding is reported, for example, in MacBeath and Schreiber, Science, 2000, 289:1760-1763, Mitchell, Nature Biotechnology, 2002, 20, 225-229 and <<Protein microarray technology>>, in Trends in Biotechnology, 2002, 20(4), 160-166.

The authors of the present invention have now developed a new method of making products of the biochip type which also has advantages over existing techniques.

The method involves the immobilization of biopolymers, which generally have a known sequence, such as DNA, proteins, oligo- or poly-saccharides, and that are carriers of a free phosphate group $(OP(O)(OH)_2)$, on a solid support having a surface covered with a metal capable of coordination bonding with the phosphate groups, such as, preferably, a solid support having a layer of metal phosphonate on the surface. The phosphate groups which act as anchoring functions may be present naturally in the polymer or may be introduced by enzymatic or chemical modification.

The anchoring is effected by ionocovalent bonding between the free phosphate group of the polymer and the metal.

This anchoring method, of the ionocovalent type, is stronger than systems bringing into play interactions of the hydrogen bonding type or of the electrostatic type (as is the case with, for example, polylysine).

The present invention therefore relates to a method of making a product of the biochip type, comprising the immobilization of at least one biopolymer carrying a free phosphate group on a solid support having a surface covered with a metal capable of coordination bonding with a phosphate group. "Solid support having a surface covered with a metal" means, in general, a support having on the surface a metal, which is preferably present in the form of a metal monolayer. Preferably, this support is a solid support coated with a layer of metal phosphonate. According to the method of the invention, the biopolymer is immobilized on the surface of the support by ionocovalent bonding between the free phosphate group of the polymer and the metal which is accessible on the surface.

The invention relates also to a product obtained by that method, namely a product of the biochip type, comprising a flat solid support having a surface covered with a metal capable of coordination bonding with a phosphate group, at least one biopolymer carrying a phosphate group being immobilized on said surface by ionocovalent bonding.

A kit for the preparation of a product as defined above also forms part of the invention. This kit comprises the following elements:
 a solid support having a surface covered with a metal capable of coordination bonding with a phosphate group;
 at least one biopolymer carrying a free phosphate group;
 optionally reagents. A solution of phosphonic acid may, for example, be useful, assuming it is desired to saturate the coordination sites on the non-targeted regions. A 1 mM solution of phosphonic acid (example: $C_4H_9PO_3H_2$) may especially be used. Advantageously, a bovine serum albumin (BSA) solution may also be used (typically a 1% by mass solution of BSA, 3% SDS in 3.5×SSC).

The invention relates also to the use of a product of the biochip type as defined above, for the purpose of screening compounds capable of binding to the immobilized biopolymer, or as an in vitro diagnostic tool.

Preparation of the Biopolymer

A "biopolymer" means a compound which is based on monomer units connected to one another generally in accordance with a known sequence, and which has biological activity or reacts with a compound having biological activity.

In particular, nucleic acids, such as RNA or DNA, especially cDNA or oligonucleotides; peptides, proteins, oligo- or poly-saccharides may be mentioned. Synthetic monomers, which do not exist in nature, may optionally be used to construct a biopolymer. From this viewpoint, for example, carbamates, phosphonates, sulfonamides and sulfoxides may be used.

PNAs (peptide nucleic acids) and aptamers may also be mentioned as other examples of biopolymers.

In general, it is possible to immobilize oligonucleotides, oligoribonucleotides or peptides which may be formed by combinatory techniques and which are endowed with recognition properties in respect of molecules of interest to be detected.

Advantageously, it is possible to prepare or obtain biopolymers that have a spacer group between the phosphate group and the body of the polymer. In the case where the polymer is a nucleic acid, it is possible to use, in particular, spacers of the polyA, polyC, polyT or polyG type (generally of approximately 10-mer, and, for example, from 7- to 9-mer), whose insertion via a synthesizer is easy. Preferably, when the polymer is a nucleic acid, such as DNA, the spacer group is a polyguanine polyG motif (namely a string of guanine units, and preferably a string of from 7 to 9 guanine units).

Preferably, the biopolymer is a nucleic acid, advantageously DNA, which is phosphorylated (namely carries a phosphate group $OP(O)(OH)_2$) in the 5' position, the phosphate group preferably being separated from the body of the nucleic acid by a polyguanine group (polyG).

This phosphorylation can be readily carried out by means of enzymes of the kinase type, for example T4 polynucleotide kinase in the presence of ATP, which T4 kinase is conventionally used in PCR reactions.

The biopolymer may also be a nucleic acid, for example DNA, which is phosphorylated (namely carries a $OP(O)(OH)_2$ group) in the 3' position, the phosphate group preferably being separated from the body of the nucleic acid by a polyguanine group (polyG). The phosphorylation in the 3' position can be carried out chemically by standard techniques relating to the chemistry of phosphoramidites.

The nucleic acids used are preferably constituted by from 25 to 70-mers (that is to say, base pairs), preferably 40-50-mers, for the oligonucleotides and from 100 to 2000 base pairs for the cDNAs.

According to another embodiment, the biopolymer is a protein, an oligo- or poly-saccharide or a peptide functionalized or modified by a phosphate group. This modification can be carried out by chemical or enzymatic methods, except of course in the case where free phosphate groups are present in nature, as is the case of peptides, proteins, and even oligo- or poly-saccharides that are already phosphorylated.

Preparation of the Support

The flat solid support chosen may be composed of any material suitable for the manufacture of chip-type products in accordance with the invention. It is possible to use, in particular, a support of glass, silicon, mica, quartz or plastics, or a support based on various synthetic polymers. The support may also be covered with a thin layer of gold. Glass supports are preferred and it is possible to use, for example, a microscope slide, and more generally any plate or sheet of glass, quartz or silicon. The shape of the support is of no importance.

In accordance with the invention, the support has a surface covered with a metal, generally in cationic form. This metal is selected to be capable of coordination bonding with a phosphate group. Zirconium is particularly suitable but there may also be mentioned by way of example other tetravalent metals, such as titanium, vanadium, tin; trivalent metals, such as aluminium, iron, chromium, gallium; an entire series of divalent metals, such as zinc, manganese, copper, cobalt, nickel; a few cases of hexavalent metals, such as molybdenum, uranium, tungsten. A recent review of the metallophosphonates summarizes these possibilities (A. Clearfield in *Progress in Inorganic Chemistry*, Vol. 47, (Ed.: K. D. Karlin), John Wiley & Sons, Inc., New York, 1998, pp. 371-510).

Preferably, the metal is deposited on the surface of the support in the form of a monolayer, preferably a monolayer of a phosphonate of said metal.

Thus, the metal may especially be bound to the surface of the support by way of a spacer molecule or arm. The latter may be, for example, a fatty acid chain carrying a phosphonate group (for example, octadecylphosphonic acid) to which the metal binds by ionocovalent bonding.

According to a particular embodiment of the invention, the spacer molecule is octadecylphosphonic acid and the metal is zirconium.

Glass sheets on which a film of the Langmuir-Blodgett type based on zirconium phosphonate rests are advantageously used, the sheets being prepared by the process such as described in Benitez et al., J. Am. Chem. Soc., 2002, 124: 4363-4370, by immersion in various aqueous solutions. In that case, the film is bound to the glass support via hydrophobic-hydrophobic interactions.

That process uses octadecylphosphonic acid which is an amphiphilic molecule which, once deposited on the surface of an aqueous phase, points its polar head $PO_3H_2$ towards the water side and its carbon chain towards the air side. By compressing those molecules, a Langmuir-Blodgeft monolayer can then be formed which may be transferred to a sheet of glass which has undergone treatment to render it hydrophobic (for example, treatment with octadecylchlorosilane). At this stage, the sheet has become hydrophilic since it is the phosphonic acid groups which are present on the surface. These groups have a strong affinity for metal ions, such as zirconium, for forming metal-$PO_3$ ionocovalent bonds.

A surface which is metallic in character and which is constituted by zirconium atoms arranged in a regular manner, generally in the form of a monolayer, is thus obtained, the Langmuir-Blodgett layer then measuring 2.4 nm thick.

The supports used in accordance with the invention have the advantage of being stable over time, and do not require necessary preactivation. They may also be stored simply in water.

The zirconium phosphonate film may also be fixed to the support in a covalent manner by proceeding as described in Katz et al., Chem. Mater., 1991, 3:699-703. A first possibility is to functionalize the glass surface by means of 3-aminopropyltrimethoxysilane which is grafted onto the surface, and the terminal $NH_2$ functions are then treated with $POCl_3$ and a base in order to introduce at the end of the chain the $PO_3H_2$ groups which are ready to receive the layer of zirconium. Another possibility is to take sheets of mica or silicon covered with a layer of gold and to treat them with 8-mercaptooctylphosphonic acid ($HS-(CH_2)_8-PO_3H_2$) which is grafted via thiol/gold coupling.

Sheets of borosilicate coated with a thin layer of gold may also be functionalized by $PO_3H_2$ terminals according to Brochsztain et al, J. Mater. Chem., 2002, 12:1250-1255, by treatment with 2-mercaptoethanol ($HS-C_2H_5-OH$) and a solution ($POCl_3$+collidine) in succession.

Immobilization of the Biopolymers

The biopolymers may be deposited on the support simply by spotting. What is usually involved is an operation of depositing microdrops (for example approximately 50 picoliters) or spots by means of a robot which takes samples from the wells of microtitration plates, for example.

The polymers are fixed by coordination bonding, of the ionocovalent type, with the metal on the surface of the support.

The spots are preferably arranged in the form of an organized network (or array). As used here, the term network or array is an ordered arrangement of biopolymer spots, as in a matrix of rows or columns. Typically, for spots approximately 150 microns in diameter and spaced by 300 microns, the spot density is of the order of 500 per $cm^2$. Preferably, the network contains more than one immobilized biopolymer.

In the context of the present invention, the expression "product or device of the biochip type" is to be understood to include any solid support on which at least one biopolymer is immobilized.

Owing to the orientation of the biopolymers substantially perpendicular to the support, it is optionally possible to immobilize these polymers at a high density, especially up to a density of $10^{10}$-$10^{12}$ polymers per $cm^2$.

The invention relates particularly to a product of the biochip type comprising a sheet of glass having a surface covered with a monolayer of zirconium octadecylphosphonate, at least one nucleic acid carrying a phosphate group in the 5' position being immobilized on said surface by ionocovalent bonding between the phosphate group of the nucleic acid and the zirconium.

Use of the Manufactured Products

The products of the biochip type manufactured in accordance with the invention have many applications, for example, they can be used for biological analyses and the screening of compounds capable of binding to the immobilized polymers.

In general, the analysis of the chips and arrays can be carried out in accordance with various techniques which are well known to the person skilled in the art (for example fluorescence, radioactivity, mass spectrometry, surface plasmon resonance, infra-red, chemiluminescence).

When the biopolymer is a nucleic acid, the products of the invention constitute high-performance tools for the in-parallel analysis of a large number of genes or DNA or RNA sequences. Their principle of operation is based on the property of hybridization or pairing of two strands of complementary sequences in order to reconstitute the DNA double helix. According to a particular embodiment, probes of oligonucleotides of known sequence, which probes are immobilized on a support substrate, are brought together with targets extracted from a biological sample to be analyzed, and are labelled using fluorescent labels.

According to a particular embodiment, in order to know where hybridization has taken place, the chip is subsequently scanned on a confocal microscope, then analyzed by quantifying the fluorescence intensity on the various spots, each of them corresponding to a given sequence.

The products of the invention are particularly suitable for studying mRNA expression profiles, nucleic acid sequences, or for searching for polymorphisms or mutations in genomic DNA, for example.

In general, the products of the invention constitute diagnostic tools that are simple and practical to use, in particular for the detection of infectious or genetic diseases.

The following Figures and Examples illustrate the invention without limiting the scope thereof.

LEGEND FOR THE FIGURES

EXAMPLES

Example 1

Immobilization of Oligonucleotides 1.1 Obtaining the Support

Figure 1:
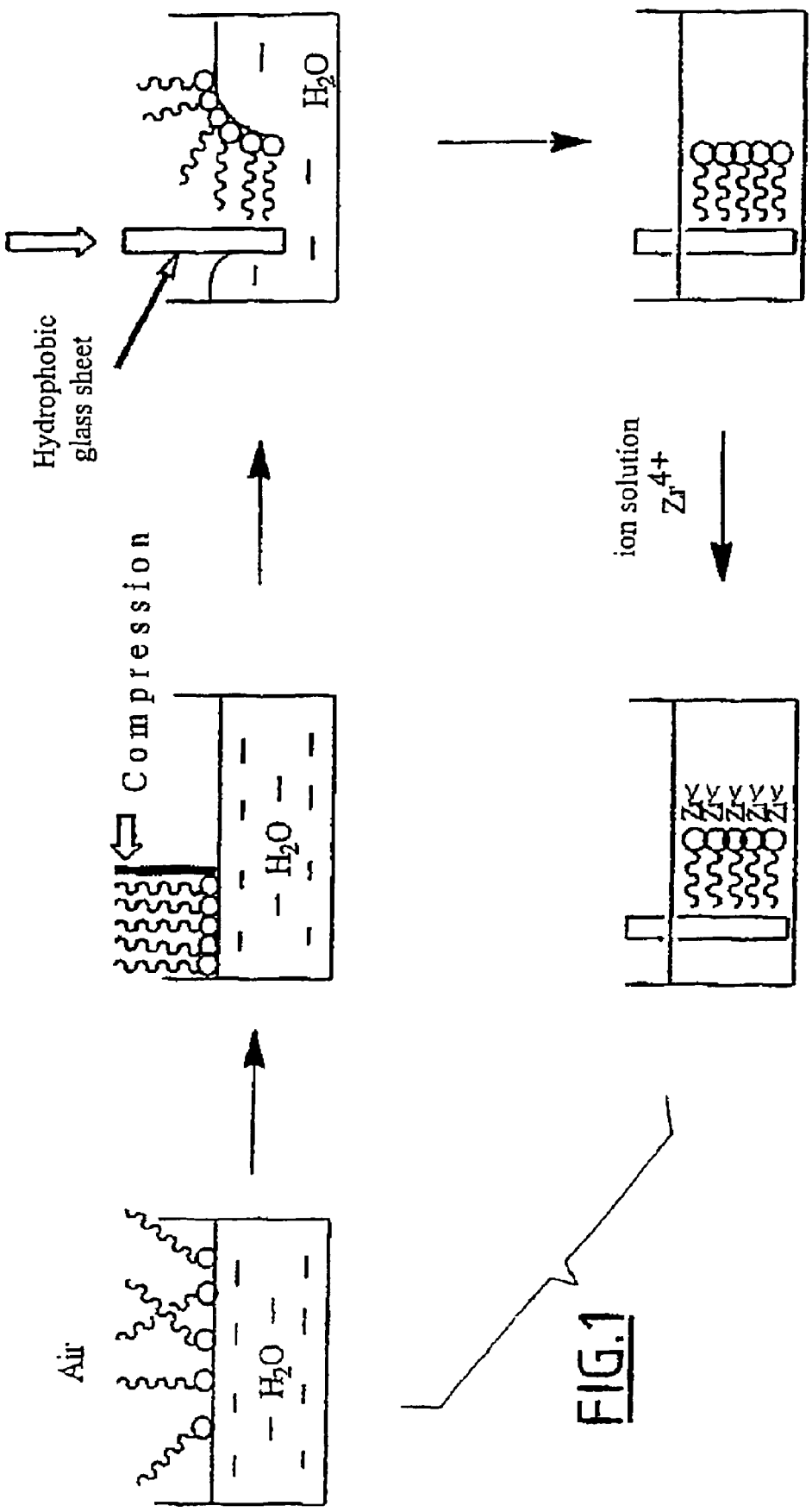
FIG. 1 is a schematic diagram showing the formation of Langmuir-Blodgett films (LB) starting from long-chain phosphonic acids. The LB film is deposited on both faces of the sheet of glass.
Figure 2:
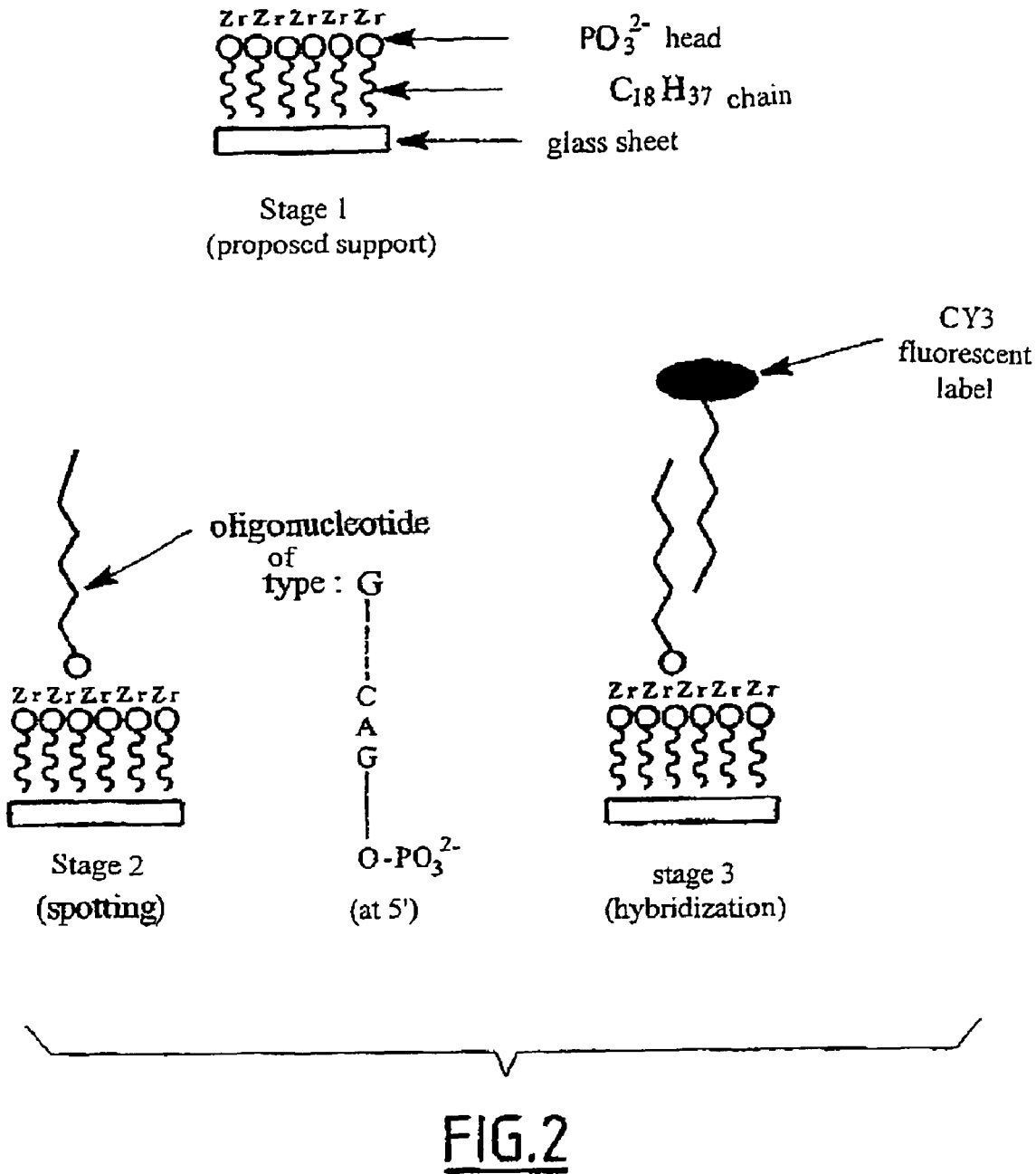
FIG. 2 shows a diagram of the anchoring of an oligonucleotide to a plate carrying a layer of zirconium phosphonate, and the use of the product obtained for a hybridization test.

Sheets of glass coated with an LB film based on zirconium phosphonate, as illustrated in FIG. 1 and as described in Benitez et al., J. Am. Chem. Soc., 2002, 124:4363-4370, are used.

The sheets of glass are then stored in ultrapure water (resistivity of approximately 18 MΩ/cm). Before use, the sheets are dried by centrifuging before being spotted by means of a robot. The two sides of the sheet can be used equally well.

1.2 Preliminary Test:

A first feasibility study showed that an oligonucleotide of 35 bases, which was phosphorylated in the 3' position and labelled in the 5' position with a CY3 fluorescent probe, anchors itself spontaneously to the Langmuir-Blodgett films based on zirconium phosphonate simply by spotting. It seems that it is indeed the terminal phosphate which is responsible for anchoring to the film since, for an identical oligonucleotide which is not phosphorylated in the 3' position, under the same spotting conditions, the quantity of probes fixed is much lower (by a factor of 5). This "non-specific" fixation is probably caused by interaction of the zirconium with the phosphodiester groups joining the nucleotide units. In addition, the fixation is stable under the standard conditions for washing DNA chips. Efficient coupling of the phosphorylated oligonucleotide compared with the non-phosphorylated homologue is therefore observed.

1.3 Oligonucleotides Used:

Four types of oligonucleotide were immobilized, namely:

a 35-mer oligonucleotide (called 1);

its analogue phosphorylated in the 5' position (called 2=1-5'-$OPO_3H_2$);

the analogue of 2 comprising a spacer group of 11 adenine units, between the oligonucleotide and the terminal phosphate group (called 3=1-$(A)_{11}$-5'-$OPO_3 H_2$); and the non-phosphorylated analogue of 3 (called 4=1-$(A)_{11}$).

1.4 Immobilization of the Oligonucleotides:

The oligonucleotides in solution in 1×SSC (pH adjusted to 6 by the addition of HCl) were spotted onto these sheets at concentrations of 50 μM, 20 μM and 5 μM.

After spotting, the sheets are dried in the open air and they are left for 24 hours in a closed box. The sheets are then rinsed for 2 minutes in 4 successive baths: 2×SSC+0.1% SDS, 1×SSC, then 0.2×SSC twice. After drying by centrifuging, the sheets are ready for hybridization.

Example 2

Hybridization Test Using the DNA Chip

Hybridization tests were carried out with the sheet of glass prepared in accordance with Example 1, on which the four types of oligonucleotide are immobilized.

For that purpose, 20 μl of a solution of the complementary 35-mer oligonucleotide labelled in the 5' position with a CY3 motif were deposited under a cover slip. The selected concentration of complementary oligonucleotide has a value corresponding to 0.002 OD unit/μl (i.e. in this case approximately 5 μM), the solvent used being a conventional hybridization mixture containing formamide, Tris EDTA buffer pH8 [tris=tris(hydroxymethyl)aminomethane], 10% SDS [SDS=sodium dodecylsulfonate] and 20×SSC buffer

[3M NaCl and 0.3M sodium citrate]. The hybridization is carried out at 42° C. overnight in hybridization chambers of the <<Arrayit>> type. When hybridization was complete, the sheets underwent washing for 2 minutes in 4 successive baths: 2×SSC+0.1% SDS, 1×SSC, then 0.2×SSC twice. After drying by centrifuging, the captured images, taking into account the fluorescence of the various spots, were analyzed using a scanner. The analysis of the images enabled the fluorescence intensity of the various spots to be quantified. The same procedure was carried out using for the hybridization a non-complementary 35-mer oligonucleotide, likewise labelled in the 5' position with a CY3 motif.

When the non-complementary oligonucleotide is used, no fluorescence is detected. When the complementary oligonucleotide is used, a fluorescence signal is observed op all of the spots, with the following characteristics:

1—Weak ground noise around the spots (dark ground).

2—The fluorescence intensity of the spots corresponding to 1 and 4 is 6 times weaker than for their homologue phosphorylated in the 5' position, for the same deposit concentration. That demonstrates the very clear favourable effect of the presence of the phosphate group for coupling the oligonucleotide to the support.

3—The fluorescence intensity of the spots corresponding to 3 is 1.6 times stronger [laser power 80%, photomultiplier power 70%: intensity 48000] than for oligonucleotide 2, for the same deposit concentration. That demonstrates the very clear favourable effect of the presence of a spacer group (11 adenine units) between the oligonucleotide and the phosphate group, enabling the oligonucleotide to be removed from the surface of the support and thus facilitating hybridization.

4—For oligonucleotides 2 and 3, the fluorescence intensities for deposit concentrations of 50, 20 and 5 µM, respectively, is 2/2/1, which shows that the optimum deposit concentration is from 20 to 5 µM.

Example 3

Chip Comprising Oligonucleotides that are Phosphorylated in the 5' Position and that are Carriers of Spacer Groups between the 5'-Terminal Free Phosphate Group and the Oligonucleotide Oligonucleotides were immobilized under the same conditions as those described in Example 1 and, before hybridization, a surface treatment was also carried out on the chip with a BSA solution (Bovine Serum Albumin: 1% BSA, 0.3% SDS in 3.5×SSC), followed by rinsing and drying, in order to improve the signal/noise ratio. The immobilization was carried out with three 33-mer oligonucleotides (called 5, 6 and 7, respectively), which had different sequences and which were phosphorylated in the 5' terminal position, and also with their analogues carrying spacers of the polyadenine (11-mer), polycytosine (11-mer), polyguanine (11-mer) or polythymine (11-mer) type between the 5'-terminal free phosphate and the oligonucleotide, which were called $(A)_{11}$-5, $(A)_{11}$-6, and $(A)_{11}$-7; $(C)_{11}$-5, $(C)_{11}$-6, and $(C)_{11}$-7; $(G)_{11}$-5, $(G)_{11}$-6, and $(G)_{11}$-7; $(T)_{11}$-5, $(T)_{11}$-6, and $(T)_{11}$-7, respectively.

Hybridization tests were carried out with those oligonucleotides in accordance with the protocol described in Example 2, using:

for oligonucleotide 5 and its analogues: a solution of the 33-mer oligonucleotide complementary to compound 5 and labelled in the 5' position with a CY3 motif;

for oligonucleotide 6 and its analogues: a solution of the 33-mer oligonucleotide complementary to compound 6 and labelled in the 5' position with a CY3 motif;

for oligonucleotide 7 and its analogues: a solution of the 33-mer oligonucleotide complementary to compound 7 and labelled in the 5' position with a CY3 motif.

Figure 3:
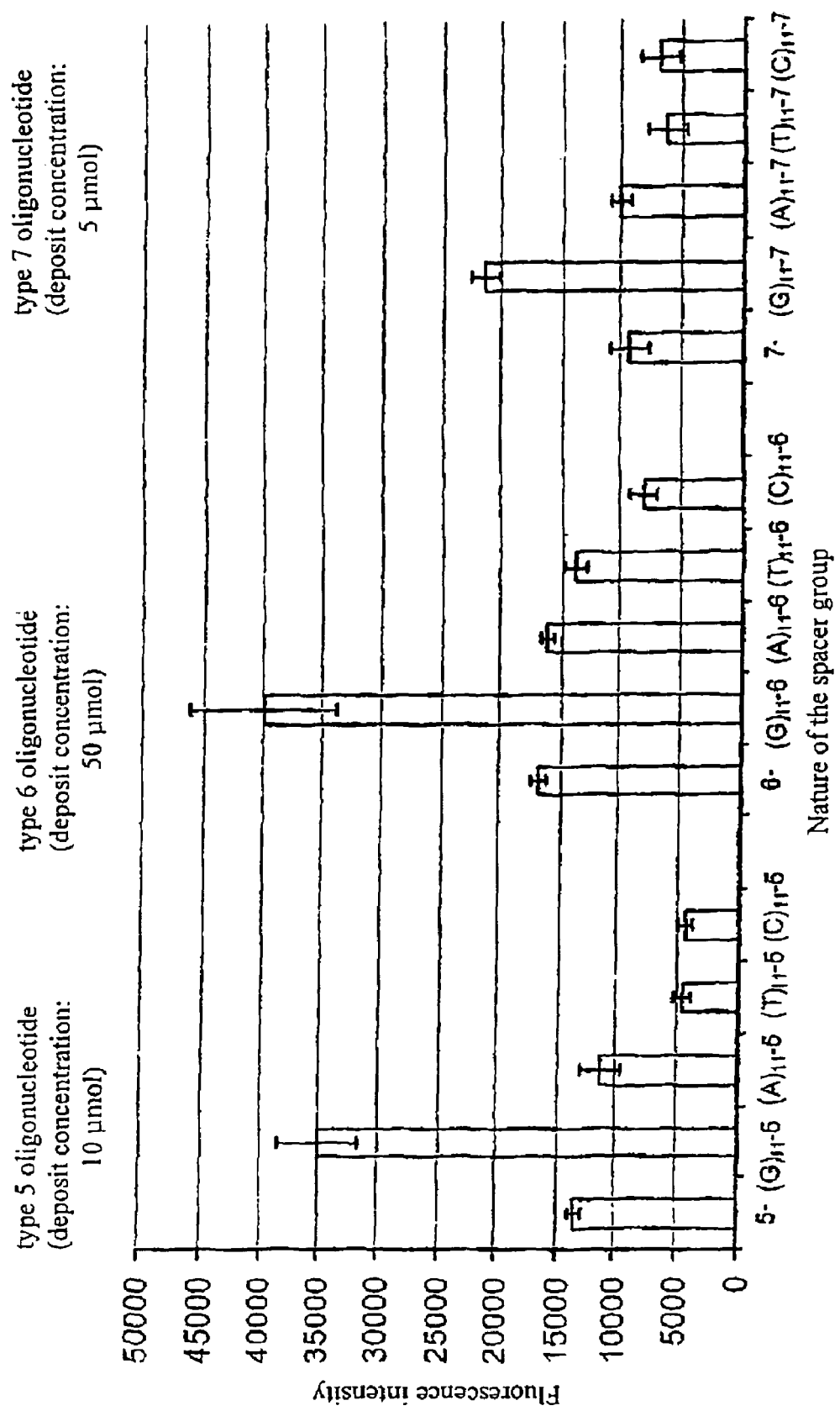
FIG. 3 is a graph showing the intensity of the fluorescence observed during tests carried out under the conditions of Example 3 described hereinafter.

Irrespective of the oligonucleotide 5, 6 or 7 tested, the fluorescence intensity of the spots corresponding to the probes provided with a (11-mer) polyguanine spacer $[(G)_{11}$-5, $(G)_{11}$-6, and $(G)_{11}$-7] is more than twice as strong as for their homologues that do not comprise a spacer group or that carry a (11-mer) polyadenine, (11-mer) polycytosine or (11-mer) polythymine spacer group, for the same deposit concentration. The appended FIG. 3 illustrates that effect, which demonstrates the very clear advantageous character of the presence of a polyguanine spacer group between the oligonucleotide and the phosphate group.

Example 4

Comparison of Properties of Chips Carrying Oligonucleotides Phosphorylated in the 5' Position, and of a Device Comprising Oligonucleotides not Carrying Terminal Free Phosphate Groups This Example used the oligonucleotides $(G)_{11}$-5, $(G)_{11}$-6 and $(G)_{11}$-7 of Example 3 and, by way of comparison, their non-modified analogues (without a polyguanine spacer or a terminal free phosphate group) called 8, 9 and 10, respectively.

Those oligonucleotides were immobilized on a support under the conditions of Example 1. Each of the oligonucleotides was spotted at a concentration of 10 micromoles per liter and then the sheets were left for 24 hours in a closed box.

Before hybridization and without preliminary rinsing, the sheets underwent treatment with a BSA solution as in Example 3. Hybridization was then carried out for 4 hours with the same complementary oligonucleotides as those mentioned in Example 3 but at a concentration of 100 nM for each of them. Irrespective of the oligonucleotide tested $[(G)_{11}$-5, $(G)_{11}$-6 or $(G)_{11}$-7], the measured fluorescence intensity of the spots is 1000 times stronger than that observed for the non-modified analogue compounds 8, 9 or 10, which illustrates, in particular, the specificity of anchoring via the terminal free phosphate group in the 5' position. In addition, the intensity of the spots for oligonucleotides $(G)_{11}$-5, $(G)_{11}$-6 and $(G)_{11}$-7 is in accordance with that observed in Example 3 (hybridization at 5 micromoles per liter), testifying in particular to the high degree of sensitivity of the chip.

The invention claimed is:

1. A biochip comprising:
   a flat solid support having a surface covered with a metal capable of coordination bonding with a phosphate group; and
   at least one nucleic acid carrying a phosphate group, OP(O)(OH)$_2$ in the 5' position being immobilized on said surface by ionocovalent bonding between the phosphate group of the nucleic acid and the metal.

2. The biochip according to claim 1, characterized in that the nucleic acid has a polyguanine (polyG) spacer group between the body of the nucleic acid and the phosphate group.

3. The biochip according to claim 1, wherein the metal is bound to the surface of the support by way of a spacer molecule.

4. The biochip according to claim 3, wherein the spacer molecule comprises a fatty acid chain carrying a phosphonate group to which the metal binds by ionocovalent bonding.

5. The biochip according to claim 1, wherein the metal is zirconium.

6. The biochip according to claim 4, wherein the spacer molecule is octadecylphosphonic acid and the metal is zirconium.

7. The biochip according to claim 1, wherein the support is glass.

8. The biochip according to claim 1, wherein:
the flat solid support is a sheet of glass having a surface covered with a monolayer of zirconium octadecylphosphonate; and the
at least one nucleic acid carrying a phosphate group in the 5' position is immobilized on said surface by ionocovalent bonding between the phosphate group of the nucleic acid and the zirconium.

9. A method for making a biochip, as defined in claim 1, comprising immobilizing at least one nucleic acid carrying a phosphate group in the 5' position on a solid support having a surface covered with a metal capable of coordination bonding with a phosphate group, the nucleic acid being immobilized on said surface by ionocovalent bonding between the phosphate group of the nucleic acid and the metal.

10. The method according to claim 9, further comprising a step of obtaining the nucleic acid carrying a phosphate group by enzymatic phosphorylation at the 5' position.

* * * * *